United States Patent [19]
Craig et al.

[11] Patent Number: 5,217,370
[45] Date of Patent: Jun. 8, 1993

[54] DENTAL APPLIANCE INFECTION CONTROL BARRIER AND DISPENSER THEREFOR

[75] Inventors: Richard Craig, Joliet; Brian L. Wilt, Frankfort, both of Ill.

[73] Assignee: Health Park Incorporated, Shorewood, Ill.

[21] Appl. No.: 640,695

[22] Filed: Jan. 14, 1991

[51] Int. Cl.⁵ .............................................. A61C 1/16
[52] U.S. Cl. ................................................. 433/116
[58] Field of Search ....................... 433/116; 211/57.1; 206/460, 495; 604/171

[56] References Cited

U.S. PATENT DOCUMENTS

| | | | |
|---|---|---|---|
| 1,539,253 | 5/1925 | Fuller | 433/116 |
| 1,742,061 | 12/1929 | Curry | 433/116 |
| 3,280,986 | 10/1966 | Nusser et al. | 211/57.1 |
| 4,394,909 | 7/1983 | Valiulis et al. | 211/59.1 |
| 4,723,912 | 2/1988 | Nieusma | 433/116 |
| 4,932,560 | 6/1990 | Roen | 211/57.1 |

Primary Examiner—Cary E. O'Connor
Attorney, Agent, or Firm—Polster, Lieder, Woodruff & Lucchesi

[57] ABSTRACT

A single use, disposable infection control barrier for use with dental appliances includes an elongate bag with a first, open end and a second, closed end so that at least a portion of a dental appliance may be inserted through the open end of the bag to the second end of the bag. The bag is transparent so as to permit a user of the dental appliance to observe the dental appliance through the bag and is flexible so as to permit the user of the dental appliance to operate the dental appliance through the bag. The bag includes a lip at the first end of the bag extending from the bag, which lip serves to guide the dental appliance into the bag. An adhesive strip is located on this lip which serves to anchor the infection control barrier to a dental appliance, if desired. A dental appliance having such an infection control barrier, a method of using such a barrier, and a dispenser package for such a barrier are also disclosed.

12 Claims, 2 Drawing Sheets

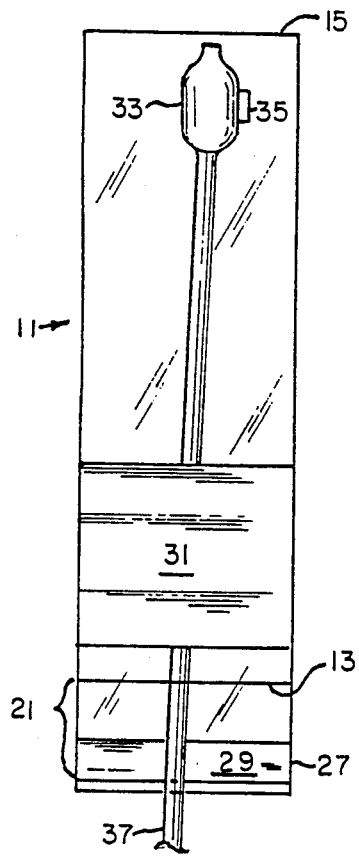
FIG.6.
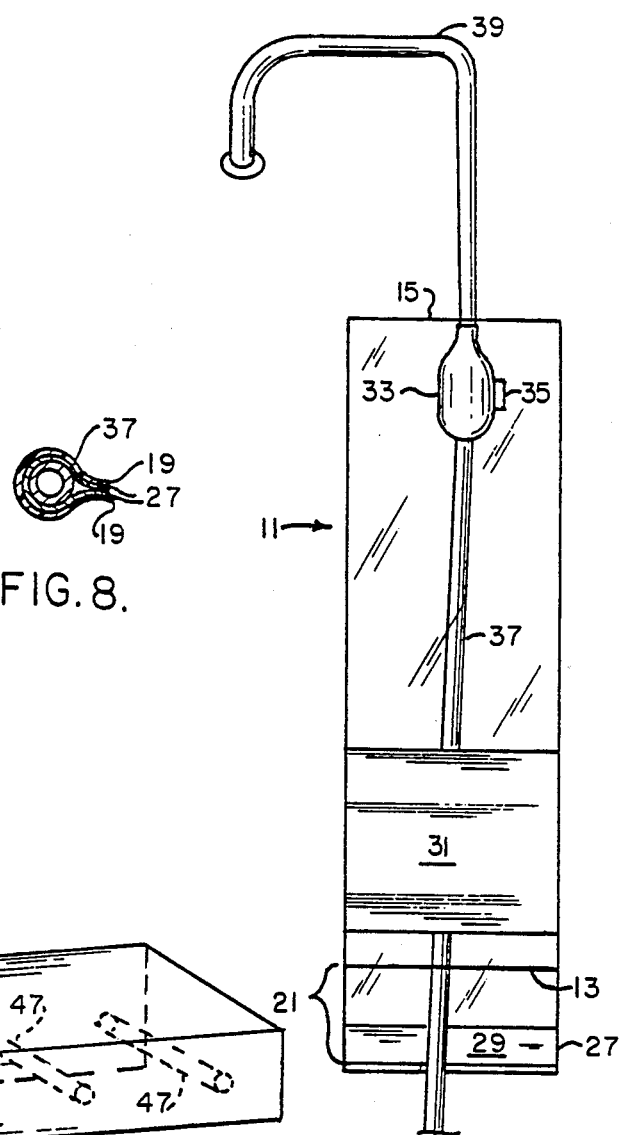
FIG.8.
FIG.7.
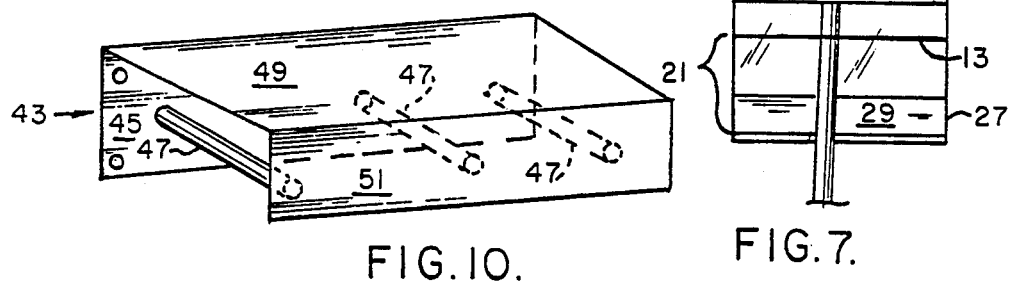
FIG.10.
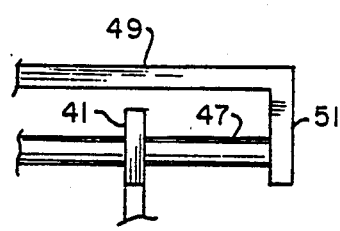
FIG.12.
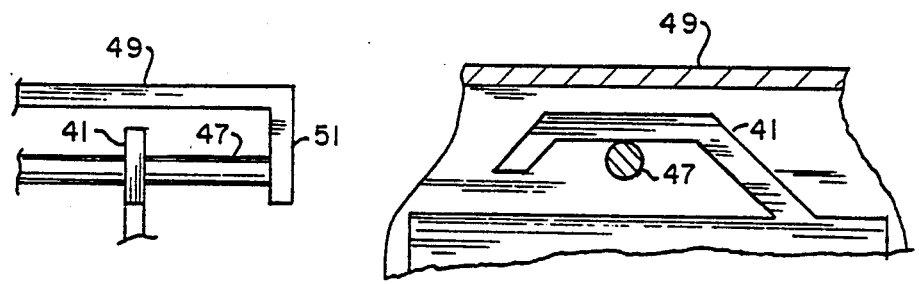
FIG.11.

000
DENTAL APPLIANCE INFECTION CONTROL BARRIER AND DISPENSER THEREFOR

BACKGROUND OF THE INVENTION

This invention relates generally to infection control and more particular to infection control devices especially suited for use by dentists.

Cross-contamination is a recognized problem in dentistry. With heightened awareness of possible viral and bacterial infections being passed from patient to patient, from dentist to patient, or from patient to dentist, it has become increasingly desirable to reduce the possibility of such cross-contamination.

One possible source of cross-contamination are the dental appliances (such as the high speed handpiece, the low suction appliance, the high suction appliance, the cavitron ultrasonic appliance, the air/water syringe appliance, and the slow speed handpiece engine and the like) which are used repeatedly on successive patients. These appliances typically are attached to a hose which runs from the appliance back to a central location. These hoses are also potential sources of cross-contamination.

Unfortunately, these appliances and hoses at present must be manually cleaned and disinfected. This is a slow, and not particularly effective process. Moreover, the biocides used to disinfect the hoses actually discolor and destroy the hoses over time, necessitating periodic replacement of these expensive hoses.

SUMMARY OF THE INVENTION

Among the various objects and features of the present invention may be noted the provision of an infection control barrier and method which greatly reduces the possibility of cross-contamination.

Another object is the provision of such an infection control barrier and method which eliminates the necessity of cleaning and disinfecting the greater portion of dental appliances and hoses between patients.

A further object is the provision of such an infection control barrier and method which provides a contamination free surface around the greater portion of dental appliances and hoses for each patient.

A fourth object is the provision of such an infection control barrier and method which eliminates the necessity of premature replacement of dental appliance hoses.

A fifth object is the provision of such an infection control barrier and method which reduces the overall expense to the dentist.

A sixth object is the provision of a dispenser for holding a large number of infection control barriers to facilitate their use by the dental professional.

Other objects and features will be in part apparent and in part pointed out hereinafter.

Briefly, a single use, disposable infection control barrier for dental appliances of the present invention includes an elongate bag having first and second ends. The first end is substantially open to permit at least a portion of a dental appliance or the like to be inserted through the open end of the bag to the second end of the bag. The second end of the bag is substantially closed to retain the portion of the dental appliance in the bag. The second end of the bag is punctured by the appliance or through other means to allow a sealed connection between the portion of the dental appliance in the bag and a portion of the appliance outside the bag. The bag is transparent so as to permit a user of the dental appliance to observe the dental appliance through the bag. The bag is also flexible so as to permit the user of the dental appliance to operate the dental appliance through the bag. The bag includes a lip at the first end of the bag extending from the bag, which lip serves to guide the dental appliance into the bag. An adhesive strip is located on this lip which serves to anchor the infection control barrier to a dental appliance, if desired.

A dental appliance with an infection control feature of the present invention includes a base of a dental appliance, a hose connected to the base, and an infection control barrier disposed over the dental appliance base and at least a part of the hose. The infection control barrier includes an elongate bag having a first, open end and a second, substantially closed end. The base of the dental appliance terminates generally at the substantially closed end of the bag, the hose extending out the open end of the bag. A dental appliance handpiece is connected through the substantially closed end of the bag to the dental appliance base. The handpiece itself is substantially disposed outside the bag.

An infection control method for dental appliances of the present invention includes the steps of inserting the base of a dental appliance through an elongate, bag-like, disposable infection control barrier from an open end of said barrier until the distal end of the base is adjacent the opposite, substantially closed end of the bag-like barrier, and puncturing the substantially closed end of the bag-like barrier. A handpiece of the dental appliance is connected to the dental appliance base so that the base remains substantially within the bag-like barrier and the handpiece remains substantially outside the bag-like barrier, creating a sealed barrier from the puncture back along the hose. After a dental procedure is performed using the dental appliance, the handpiece is removed from the base, and the base is removed from the bag-like barrier. The above steps are repeated for successive patients.

An infection control barrier dispenser package of the present invention includes a plurality of infection control barriers, which barriers are carried on at least one hook. A plurality of barriers are connected to each hook, each barrier having a perforated line between it and its associated hook so that each barrier is individually removable from its associated hook. A dispenser for the infection control barriers has a plurality of rods extending parallel to each other. Each hook is disposed to fit over one rod so as to hold the barriers in place in the dispenser. The dispenser further includes structure for retaining the hooks in place on the rods. The dispenser constitutes a central setup station for ease of organization, storage and dispensing of infection control barriers. Without the dispenser, it is very difficult to keep a large number of infection control barriers organized. The dispenser of the present invention provides this organization simply and efficiently.

BRIEF DESCRIPTION OF THE DRAWINGS

FIGS. 4-7 are front elevations illustrating the use of the infection control barrier of FIG. 1;

FIG. 8 is a cross-sectional view illustrating the anchoring of the infection control barrier of FIG. 1 to the hose of a dental appliance;

FIG. 10 is a perspective view of a dispenser used with hooks like that shown in FIG. 9;

FIG. 11 is a cross-sectional view illustrating the placement of the hook of FIG. 9 on the dispenser of FIG. 10; and FIG. 12 is a side elevation, with parts broken away for clarity, of the hook of FIG. 9 on the dispenser of FIG. 10.

Similar reference characters indicate similar parts throughout the several views of the drawings.

DESCRIPTION OF THE PREFERRED EMBODIMENT

Turning now to the drawings, an infection control barrier 11 of the present invention is designed to be single use and disposable when used with various dental appliances and the like. The infection control barrier is an elongate polyethylene (or other suitable plastic) bag. By way of illustration and not by way of limitation, the bag may be a 12" side-seal polyethylene bag, 3" in width with a 1" lip. Wall thickness, again not by way of limitation, is 1.5 mil.

Figure 2:
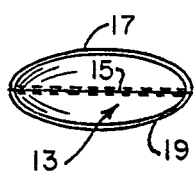
FIG. 2 is a top plan, with parts separated for clarity, of the infection control barrier of FIG. 1.

Bag 11 has a first, open end 13, and a second, closed end 15 (best illustrated in FIG. 2, in which the front 17 and back 19 of bag 11 have been spread apart to illustrate that end 13 of the bag is open). Sealed end 15 in the preferred embodiment is achieved by folding a single piece of plastic over at end 15 and then performing a side-sealing operation to form bag 11.

A 1" lip 21 formed as a continuation of back wall 19 extends from open end 13 to a perforated line 23. Line 23 separates bag 11 from a header 25, which is used to connect a plurality of bags 11 together (explained below). Bag 11 may be readily removed from header 25 by tearing the two apart along perforated line 23.

Figure 3:
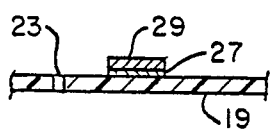
FIG. 3 is a cross-sectional view, on an enlarged scale, with parts further enlarged for clarity, taken along lines 3—3 of FIG. 1.

Lip 21 has disposed thereon an adhesive strip 27 which is covered by a peel-off strip 29 (FIG. 3) before use.

Bag 11 is flexible and transparent, except for a portion 31 which is imprinted with a colored or non-transparent block on both sides of the bag. This colored section allows for ease of recognition since the otherwise clear bags are difficult to see when dropped.

Figure 1:
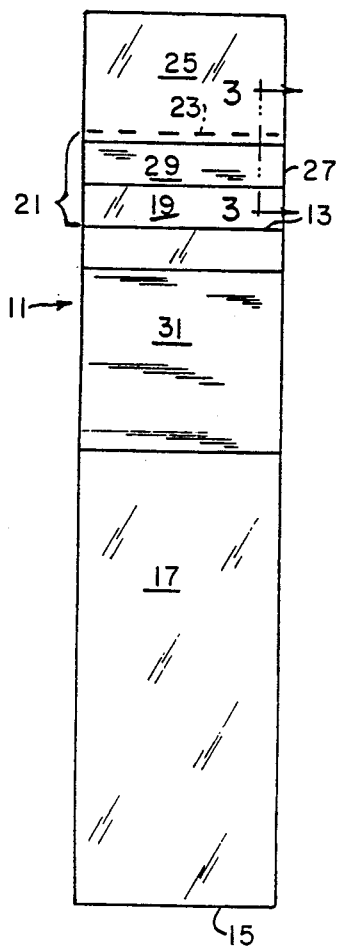
FIG. 1 is a front elevation of an infection control barrier of the present invention.
Figure 4:
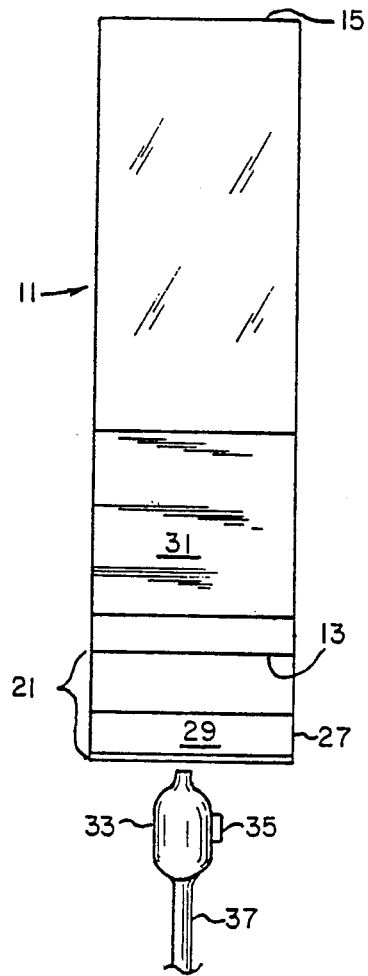
Figure 5:
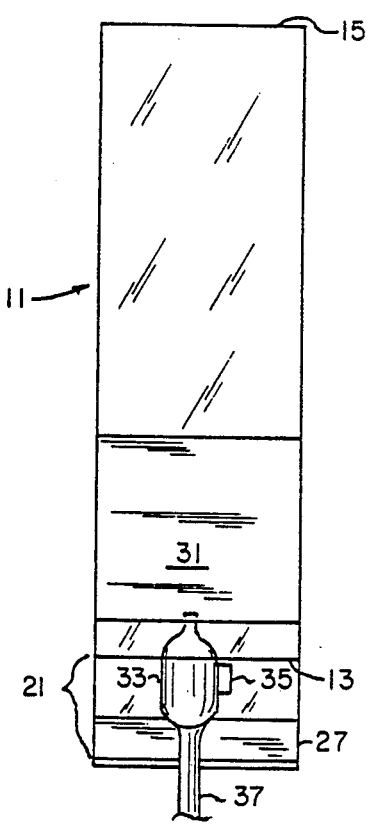

Use of infection control barrier 11 is illustrated in FIGS. 4-8. In use the bags are torn off from header 25 and inverted from the position shown in FIG. 1. A dental appliance, in this case the base 33 of a dental appliance having a control switch 35 and attached to a hose 37 is brought up to the lower, open end 13 of bag 11. Lip 21 serves to guide the dental appliance 33 into bag 11, as shown in FIG. 5. The appliance and connected hose 37 are then inserted into the bag until the distal end of the appliance is disposed adjacent the closed end 15 of bag 11 (see FIG. 6). Then the closed end 15 is punctured (either by the appliance itself, a disposable tip or by external means as desired) so that a handpiece 39 (FIG. 7) may be secured to appliance base 33. In this way, the closed end of bag 11 retains the appliance base in place and protects it as well as a considerable length of hose from contamination.

After the appliance is properly positioned in bag 11, peel-off strip 29 is removed, and the adhesive strip 27 is used to secure the lip of the bag to the hose 37, as illustrated in FIG. 8. This anchors the infection control barrier to the hose. Of course, the adhesive used is selected to permit the barrier to be removed from the hose after use.

Since bag 11 is transparent, it permits a user of the dental appliance to observe the placement of the dental appliance through the walls of the bag. Moreover, the bag is flexible so that the dental professional may operate switch 35 to control the dental appliance.

Alternatively, the portion of the dental appliance disposed in the barrier 11 is the engine of the slow speed handpiece, for example. Protecting the engine of the handpiece is significant because the engine is expensive and susceptible to damage from sterilization. Use of barrier 11 protects the slow speed engine so that it need not be sterilized, thereby preventing the possible damage otherwise resulting from sterilization.

From the above, it should be appreciated that the method of the present invention includes the steps of inserting the base of a dental appliance, such as base 33, through open end 13 of infection control barrier 11 until the distal end of the base is adjacent the opposite, substantially closed end 15 of the barrier. The closed end is punctured and a handpiece, like handpiece 39, of the dental appliance is connected to the dental appliance base so that the base remains substantially within the bag-like barrier and the handpiece remains substantially outside the bag-like barrier 11. After a dental procedure is performed using the dental appliance, the handpiece is removed from the base, and the base and attached hose are removed from the barrier. This provides complete contamination protection from the appliance base to about 12" down the hose. Each step is repeated for successive patients.

It should be noted that by replacing barriers 11 between each patient, the barriers used are clean for every patient. The barriers further provide protection for the appliance bases and hoses from contaminated blood and saliva and other debris which would otherwise require the appliance base and hose to be thoroughly cleaned and disinfected.

Figure 9:
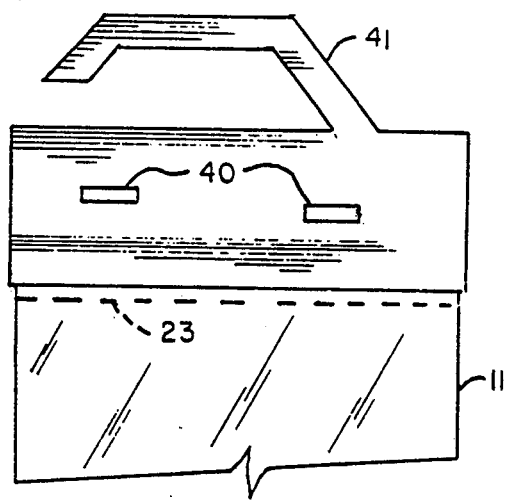
FIG. 9 is a front elevation of a hook device used to hold a plurality of infection control barriers of FIG. 1.

To facilitate the use of infection control barrier 11, they are stapled in groups of 100 by staples 40 to a cardboard hook 41 (FIGS. 9 and following). Hook 41 holds a group of barriers 11 together until needed. When one or more barriers are needed, they are simply removed by tearing along perforated line 23.

Hook 41 is designed to be used with a dispenser 43 (FIG. 10) which holds a number of hooks 41. Dispenser 43 has a back plate 45 for wall-mounting and a plurality of support rods 47 at evenly-spaced intervals. Extending forwardly from back plate 45 is a top cover 49 which (see FIG. 11) captures hook 41 at the top. Similarly, a front cover 51 extending downwardly from top cover 49 captures hook 41 to keep it from sliding off the front of its rod 47. A number of hooks 41 can be supported by a single rod 47. The open-side hook design allows one hook, with its associated barriers or an empty hook, to be easily removed without having to remove all the hooks which are in front of it on that particular support rod 47. Moreover, because of perforation lines 23, each barrier 11 is individually removable from its associated hook 41.

In view of the above, it will be seen that the various objects and features of the invention are achieved and numerous advantageous results obtained. The examples of the invention given herein shall be construed as illustrative and not in a limiting sense.

What is claimed is:

1. A single use, disposable infection control barrier for use with dental appliances and the like, comprising:

an elongate bag having first and second ends, the first end being substantially open to permit at least a portion of a dental appliance or the like to be inserted through the open end of the bag to the second end of the bag, the second end of the bag being closed yet puncturable to retain said portion of the dental appliance in the bag while allowing communication, through the puncture, of that portion of the dental appliance retained in the bag with another portion of the dental appliance disposed outside the bag;

said bag being transparent so as to permit a user of the dental appliance to observe the dental appliance through the bag;

said bag being flexible so as to permit the user of the dental appliance to operate the dental appliance through the bag;

said bag including a flexible lip at the first end of the bag extending from the bag and unitary therewith, said lip extending only partially around the open end of the bag, said lip serving to guide the dental appliance into the bag.

2. The infection control barrier as set forth in claim 1 wherein the bag is polyethylene.

3. The infection control barrier as set forth in claim 1 wherein the bag further includes an adhesive strip on the lip so as to permit the user to secure the bag to the dental appliance once said appliance is inserted to a desired position in the bag.

4. The infection control barrier as set forth in claim 3 wherein the adhesive strip is covered, prior to use, by a peel-off strip.

5. The infection control barrier as set forth in claim 1 wherein the bag further includes a flexible, non-transparent layer disposed toward the open end of the bag.

6. The infection control barrier as set forth in claim 1 further including a header for the bag, said bag being attached to the header at a perforated line such that the bag may readily be removed from the header by tearing along the perforated line without opening the closed end of the bag.

7. A dental appliance with an infection control feature comprising:

a base of a dental appliance;

a hose connected to said base;

an infection control barrier disposed over the dental appliance base nd at least a part of the hose, said infection control barrier consisting essentially of an elongate flexible bag having a first, open end and a second, substantially closed end, the base of the dental appliance terminating generally at the substantially closed end of the bag, the hose extending out the open end of the bag;

said bag being transparent so as to permit a user of the dental appliance to observe the base of the dental appliance through the bag, said bag being flexible so as to permit the user of the dental appliance to operate the dental appliance through the bag, said bag including a flexible lip at the first end of the bag extending from the bag and unitary therewith, said lip extending only partially around the open end of the bag, said lip serving to guide the base of the dental appliance into the bag; and a dental appliance handpiece connected through the substantially closed end of the bag to the dental appliance base, said handpiece being disposed substantially outside the bag.

8. The dental appliance as set forth in claim 7 wherein the infection control barrier further includes an adhesive strip disposed on the bag generally at the open end thereof, said strip securing the bag to one of the base or the hose.

9. An infection control method for dental appliances comprising:

inserting the base or engine of a dental appliance through an elongate, totally flexible, bag-like, disposable infection control barrier from an open end of said barrier until an distal end of an base is adjacent the opposite, closed end of the bag-like barrier;

said bag-like barrier being transparent so as to permit a user of the dental appliance to observe the base of the dental appliance through the barrier, being flexible so as to permit the user of the dental appliance to operate the dental appliance through the barrier, and including a flexible lip at the first end thereof extending from the bag-like barrier and being unitary therewith, said lip extending only partially around the open end of the bag, said lip serving to guide the base of the dental appliance into the bag;

puncturing the closed end of the bag-like barrier;

connecting a handpiece of the dental appliance to the dental appliance base so that the base remains substantially within the bag-like barrier and the handpiece remains substantially outside the bag-like barrier;

after a dental procedure is performed using the dental appliance, removing the handpiece from the base, and removing the base from the bag-lie barrier; and repeating the above steps for successive patients.

10. An infection control barrier dispenser package comprising:

a plurality of infection control barriers, said barriers being carried on at least one hook, a plurality of barriers being connected to each hook, each barrier having a perforated line between it and its associated hook so that each barrier is individually removable from its associated hook; and a dispenser for said infection control barriers, said dispenser having a plurality of rods extending parallel to each other, each hook being disposed to fit over one rod so as to hold the barriers in place in the dispenser, said dispenser further including means for retaining the hooks in place on the rods;

each infection control barrier comprising an elongate bag having first and second ends, the first end being substantially open to permit at least a portion of a dental appliance or the like to be inserted through the open end of the bag to the second end of the bag, the second end of the bag being closed yet puncturable to retain said portion of the dental appliance in the bag while allowing communication, through the puncture, of that portion of the dental appliance retained in the bag with another portion of the dental appliance disposed outside the bag;

said bag being transparent so as to permit a user of the dental appliance to observe the dental appliance through the bag;

said bag being flexible so as to permit the user of the dental appliance to operate the dental appliance through the bag;

said bag including a flexible lip at the first end of the bag extending from the bag and unitary therewith, said lip extending only partially around the open end of the bag, said lip serving to guide the dental appliance into the bag.

11. The infection control barrier dispenser package as set forth in claim 10 wherein the dispenser includes a base plate, said rods extending outwardly from the base plate, said retaining means including a top cover extending outwardly from the base plate a distance substantially the same as the length of the rods.

12. The infection control barrier dispenser package as set forth in claim 11 wherein the retaining means further includes a front cover extending generally downwardly from the top cover, said front cover being disposed generally adjacent the ends of the rods opposite the base plate.

* * * * *

UNITED STATES PATENT AND TRADEMARK OFFICE
CERTIFICATE OF CORRECTION

PATENT NO.    : 5,217,370
DATED         : June 8, 1993
INVENTOR(S)   : Richard Craig, et al It is certified that error appears in the above-indentified patent and that said Letters Patent is hereby corrected as shown below:

On the Title Page, Delete Assignee: "Health Park, Incorporated" and insert -- Assignee: Health Pak, Incorporated --

Signed and Sealed this

Fifteenth Day of November, 1994

Attest:

BRUCE LEHMAN

Attesting Officer  Commissioner of Patents and Trademarks